US005866619A

United States Patent [19]
Sintov et al.

[11] Patent Number: 5,866,619
[45] Date of Patent: Feb. 2, 1999

[54] COLONIC DRUG DELIVERY SYSTEM

[75] Inventors: Amnon Sintov; Abraham Rubinstein, both of Jerusalem, Israel

[73] Assignees: Perio Products Ltd.; Yissum Research Development Company of the Hebrew University of Jerusalem, both of Israel

[21] Appl. No.: 969,706

[22] Filed: Nov. 26, 1997

Related U.S. Application Data

[63] Continuation of Ser. No. 481,148, Jun. 7, 1995, abandoned, which is a continuation of Ser. No. 193,775, Feb. 10, 1994, Pat. No. 5,525,634, which is a continuation of Ser. No. 694,293, May 2, 1991, abandoned, which is a continuation-in-part of Ser. No. 518,714, May 4, 1990, abandoned.

[51] Int. Cl.$^6$ ............... A61K 9/48; A61K 9/64; A61K 9/36; A61K 9/50
[52] U.S. Cl. ............ 514/777; 514/960; 514/965; 424/426; 424/456; 424/458; 424/463; 424/464; 424/479; 424/493; 424/499
[58] Field of Search ............... 514/777, 960, 514/965; 424/426, 456, 458, 463, 464, 479, 493, 499

[56] References Cited

U.S. PATENT DOCUMENTS

| | | | |
|---|---|---|---|
| 4,432,966 | 2/1984 | Zeitoun et al. | 424/21 |
| 4,627,850 | 12/1986 | Deters et al. | 604/892 |
| 4,863,744 | 9/1989 | Urquhart et al. | 424/484 |
| 4,904,474 | 2/1990 | Theeuwes et al. | 424/424 |

FOREIGN PATENT DOCUMENTS

| | | |
|---|---|---|
| 28876/89 | 8/1989 | Australia . |
| 31604/89 | 10/1989 | Australia . |
| 35718/89 | 11/1989 | Australia . |
| 35747/89 | 11/1989 | Australia . |
| 40126/89 | 3/1990 | Australia . |
| 0 280 571 | 8/1988 | European Pat. Off. . |
| 0 450 176 | 10/1991 | European Pat. Off. . |
| 2 306 710 | 11/1976 | France . |
| 27 17 707 | 10/1978 | Germany . |
| 1 538 123 | 1/1979 | United Kingdom . |
| 2 174 599 | 11/1986 | United Kingdom . |
| 2220350 | 1/1990 | United Kingdom . |
| WO 89/08119 | 9/1989 | WIPO . |

OTHER PUBLICATIONS

Bartalsky, A., "Salicylazobenzoic Acid In Ulcerative Colitis," *Lancet* 1:960 (1982).
Brown, J.P. et al., "A Polymeric Drug for Treatment of Inflammatory Bowel Disease," *J. Med. Chem.* 26:1300–1307 (1983).
Cummings, J.H. et al., "Fermentation in the human large intestine and the available substrates," *Am. J. Clin. Nutr.* 45:1243–1255 (1987).
Cummings, J.H., "Progress report: Laxative abuse," *Gut* 15:758–766 (1974).
Fairbairn, J.W., "The Active Constituents Of The Vegetable Purgatives Containing Anthracene Derivatives," *J. Pharm. Phanrmacol.* 1:683–694 (1949).
Friend, D.R. et al., "A Colon–Specific Drug–Delivery System Based on Drug Glycosides and the Glycosidases of Colonic Bacteria," *J. Med. Chem.* 27:261–266 (1984).

(List continued on next page.)

*Primary Examiner*—Carlos A. Azpuru
*Attorney, Agent, or Firm*—Sterne, Kessler, Goldstein & Fox P.L.L.C.

[57] ABSTRACT

A colonic delivery system for delivering a drug to the colon is provided. The system comprises a drug in combination with a matrix, wherein the matrix comprises a saccharide-containing polymer. According to the invention, the matrix is resistant to chemical and enzymatic degradation in the stomach and small intestine. The matrix is degraded in the colon by bacterial enzymatic action, and the drug is released. The system is useful for targeting drugs to the colon in order to treat colonic disease. The system is also useful for enteric administration of drugs such as proteins and peptides which are otherwise degraded in the stomach and small intestine.

28 Claims, 8 Drawing Sheets

OTHER PUBLICATIONS

Friend, D.R. et al., "Drug Glycosides: Potential Prodrugs for Colon–Specific Drug Delivery," *J. Med. Chem.* 28:51–57 (1985).

Gassmann, B. et al., "Pharmaceutical composition with delayed activity release," *Chemical Abstracts* 103 (22), Abstract No. 183574c (1985).

Gullikson, G.W. et al., "Mechanisms of Action of Laxative Drugs," in Csaky, T.Z., ed., *Pharmacology of Intestinal Permeation II*, Springer–Verlag, Heidelberg, pp. 419–459 (1984).

Hardcastle, J.D., et al., "The action of sennosides and related compounds on human colon and rectum," *Gut* 11:1038–1042 (1970).

Kltoz, U., "Clinical Pharmacokinetics of Sulphasalazine, Its Metabolites and Other Prodrugs of 5–Aminosalicylic Acid," *Clin. Pharmacokinetics* 10:285–302 (1985).

Lancaster, C.M. et al., "Drug delivery to the colon: polymer susceptibility to degradation by colon contents," *Polymer Prep.* 30:480–481 (Jan. 1989).

Levine, D.S. et al., "Coating of Oral Lomethasone Dipropionate Capsules With Cellulose Acetate Phthalate Enhances Delivery of Topically Active Antiinflammatory Drug to the Terminal Ileum," *Gastroentrol.* 92:1037–1044 (1987).

Mardini, H.A. et al., "Effect of polymer coating on faecal recovery of ingested 5–amino salicylic acid in patients with ulcerative colitis," *Gut* 28:1084–1089 (1987).

Mirelman, D. et al., "Effects of Covalently Bound Silica–Nitroimdazole Drug Particles on *Entamoeba histolytica*," *J. Infect. Dis.* 159(2):303–309 (Feb. 1989).

Moretó, M. et al., "3,3–Bis–(4–hydroxyphenyl)–7–methyl–2–idolinone (BHMI), the Active Metabolite of the Laxative Sulisatin," *Arzneim.–Forsch./Drug Res.* 29(II)(10):1561–1564 (1979).

Rachmilewitz, D., "Coated mesalazine (5–aminosalicylic acid) versus sulphasalazine in the treatment of active ulcerative colitis: a randomised trial," *Brit. Med. J.* 298:82–86 (Jan. 14, 1989).

Rasmussen, S.N. et al., "5–Aminosalicylic Acid in a Slow–Release Preparation: Biovailability, Plasma Level, and Excretion in Humans," *Gastroenterol.* 83:1062–1070 (1982).

Rubinstein, A., "Microbially Controlled Drug Delivery To The Colon," *Biopharm. & Drug Dispos.* 11(6):465–475 (Aug.–Sep. 1990).

Saffran, M. et al., "A New Approach to the Oral Administration of Insulin and Other Peptide Drugs," *Science* 233:1081–1084 (1986).

Saffran, M. et al., "Oral Insulin in Diabetic Dogs," *Diabetes* 38(S2):81A, Abstract No. 324 (May 1989).

Saffran, M. et al., "Vasopressin: A Model for the Study of Effects of Additives on the Oral and Rectal Administration of Peptide Drugs," *J. Pham. Sci.* 77(1):33–38 (1988).

Salyers, A.A., "Energy sources of major intestinal fermentative anaerobes," *Am. J. Clin. Nutr.* 32:158–163 (1979).

Salyers, A.A. et al., "Cellular Location of Enzymes Involved in Chondroitin Sulfate Breakdown by *Bacteroides thetaiotaomicron*" *J. Bacteriol.* 143(2):772–780 (1980).

Simpkins, J.W. et al., "Evidence for the Delivery of Narcotic Antagonists to the Colon as their Glucuronide Conjugates," *J. Pharmacol. Exper. Therap.* 244(1):195–205 (1988).

Willoughby, C.P. et al., "Distribution and metabolism in healthy volunteers of disdium azodisalicylate, a potential therapeutic agent ulcerative colitis," *Gut* 23:1081–1087 (1982).

R. Laakso, et al., "Effects of core components on indomethacin release from film–coated granules," *Int. J. Pharm.* 67:79–88 (Jan. 1991).

Lancaster et al., Drug delivery to the Colon: Polymer susceptibility to Degradation by Colon Contents, Polymer. Prepr. 30:480–1 (1989).

COLONIC DRUG DELIVERY SYSTEM

This application is a continuation; application Ser. No. 08/481,148, filed Jun. 7, 1995, now abandoned; which is a continuation of application Ser. No. 08/193,775, filed Feb. 10, 1994 now U.S. Pat. No. 5,525,634; which is a continuation of application Ser. No. 07/694,293, filed May 2, 1991 now abandoned; which is a continuation-in-part of application Ser. No. 07/518,714, filed May 4, 1990 now abandoned.

FIELD OF THE INVENTION

The invention is directed to a drug delivery system for the delivery of enterally administered pharmaceuticals to the large bowel.

BACKGROUND OF THE INVENTION

Specific delivery of drugs and pharmaceutical compositions to the colon is important in the treatment of a wide variety of diseases and conditions. Targeting of drugs to the colon provides the ability to locally treat large bowel diseases, thus avoiding systemic effects of drugs or inconvenient and painful transcolonic administration of drugs. Furthermore, there is an increased need for delivery to the colon of drugs that are reported to be absorbable in the colon, such as steroids, which would increase the efficiency and enable to reduce the required effective dose (Dogbillon, J., et al., *Br. J. Clin. Pharmacol.* 19:113S (1985); Antonin, K. H. et al., *Br. J. Clin. Pharmacal.* 19:137S (1985); Fara, J. W., 3rd *International Conference on Drug Absorption*, Edinburgh (1988); for a review see Rubinstein, A., *Biopharm. Drug Dispos.* 11:465–475 (1990)).

However, the targeting of drugs to desired locations in the alimentary canal can be complicated. Because of its location at the distal portion of the alimentary canal, the colon is particularly difficult to access. The design of orally administered colonic delivery systems must take into account factors such as the pH of the alimentary canal and the presence of enzymes in the stomach and small intestine.

In current techniques for targeting drugs to the colon, solid formulations of the desired drug molecules are coated with a pH resistant polymeric coating. Such formulations are similar to enteric coated formulations which may be used to deliver drugs to the distal ileum. Enteric coatings include bioerodable polymers such as shellac and cellulose acetate phthalate. (Levine et al., *Gastroenterology* 92:1037–1044 (1987)).

In contrast to the enteric coated formulations, however, the formulations for colonic delivery are designed to withstand both low and slightly basic pH values (around seven) for several hours. During this time, they are assumed to pass the stomach and the small intestine and reach the large intestine, where the coat disintegrates and the drug release process is initiated. In this way, drugs such as 5-amino salicylic acid (5-ASA), and some steroids have been delivered to the colon.

The polymers used for this purpose are commonly acrylic acid derivatives or cellulose derivatives such as cellulose acetate phthalate, or ethyl cellulose (Rasmussen, S. N., et al., *Gastroenterology* 83:1062 (1982); Levine, D. S., et al., *Gastroenterology* 92:1037 (1987)); Mardini H., et al., *Gut* 28:1084–1089 (1987). However, an important limitation of this technique is the uncertainty of the location and environment in which the coat starts to degrade. Depending upon the gastrointestinal motility pattern, which can vary widely in individual patients and in different disease states, degradation of the coating can occur deep in the colon, or within the small intestine.

The presence of short chain fatty acids, carbon dioxide, and other fermentation products, and residues of bile acids, often reduce the pH of the colon to approximately six (Stevens, C. E., *Amer. J. Clin. Nutr.* 31:S161 (1978); McNeil, N. I., et al., *Gut* 28:707 (1987)). This change in pH calls into question the reliance on higher colonic pH as a trigger. U.S. Pat. No. 4,627,850 (Ditter et al.) discloses an a osmotic capsule for the controlled rate delivery of a drug comprising outer and inner walls each formed of a different polymeric material, the inner wall defining a space containing the drug, with a passageway through the walls connecting the exterior of the outer wall with the interior of the inner wall. U.S. Pat. No. 4,904,474 (Theeuwes et al) discloses a colonic drug delivery device comprising means for delaying the delivery in the drug and in the small intestine and means for delivering the drug in the colon. This device comprises osmotic means for forcing the active pharmaceutical agent out from the compartment in which it is contained through an exit provided in said compartment, into the colon. The means for delaying delivery in the stomach or in the small intestine are practically pH resistant coatings. The delay in delivery of the drug is time based, the structure is so calculated that the contents of the inner drug-filled space are not forced out before the device has reached the preselected target region of the gastrointestinal tract. One of the drawbacks of these devices is that in case the travel of the device in the GI tract is delayed in a certain portion of the tract, for example due to mechanical reasons, the drug will still be released after the predetermined time has passed, irrespective of the fact that the target region has not been reached.

The ability of the colonic flora to degrade substrates that are resistant to small bowel digestion has been studied as an alternative method for colonic delivery of drugs. This principle was utilized to deliver laxative products, mainly sennoside and related compounds. Concentrated senna extract contains anthracene derivatives which exist in the form of glycosides and can be hydrolyzed to anthroquinones, anthranols, and oxanthrones. The sennosides are much more effective as laxatives when administered intact, compared to the sugar-free aglycones, probably because the sugar moiety provides protection against chemical breakdown in the small intestine (Fairbairn, J. W., *J. Pharm. Pharmacol.* 1:683 (1949)). Hardcastle and Wilkins demonstrated that when sennosides were directly administered to the colon, no laxative activity was observed as compared to administration of the same compounds previously incubated with feces or *E. coli*. It was postulated that bacteria liberate the free anthraquinones, which then promote colonic peristalsis via a local effect on the mysenteric plexus (Hardcastle, J. D., et al., *Gut* 11:1038 (1970); Cummings, J. H., *Gut* 15:758 (1974)).

Bacteria can also act on the phenolic laxative sulisatin, in which two of the phenols are esterified with sulfate. The lack of arylsulfatase activity in the small intestinal mucosa allows the drug to pass intact to the colon, where bacteria convert it to the active hydroxy and dihydroxy derivatives. This is in contrast to the acetate ester of the diphenylmethane derivative bisacodyl, which is readily cleaved by the esterases in the small intestine to an active metabolite, which in turn stimulates water and electrolyte secretion from the colonic mucosa and results in laxation (Cummings, J. H., *Gut* 15:758 (1974); Moreto, M., et al., *Arzneim. Forsch./Drug Res.* 29:1561 (1979); Gullikson, G. W., et al., in *Pharmacology of Intestinal Permeation II*, Csaky, T. Z. (ed.), Springer-Verlag, Heidelberg, p. 419 (1984)).

Simpkins and co-workers recently compared the ability of the narcotic antagonists naloxone and nalmefene with their glucuronide conjugates to induce diarrhea in morphine-dependent rats. (In these animals the brain is sensitive to narcotic antagonists, and the animals are useful in the bioassay of the systemic delivery of narcotic antagonists intended for local colonic release.) Oral administration of the two drugs caused diarrhea, withdrawal behavior and tail skin temperature response within 15 minutes, while with the glucuronide conjugates of either of the narcotic antagonists diarrhea was delayed for 1 to 3 hours, reflecting the transit time to the distal ileum. Direct colonic administration of the naloxone and nalmefene glucuronides caused diarrhea with 5–8 minutes. It was suggested that the pharmacologic response to the glucuronide conjugates of naloxone and nalmefene was initiated by bacterial β-glucuronidases in the rat colon. This hydrolysis of the drug glucuronides was found to be specific to bacterial activity in the colon, because the glucuronides were inactive when administered subcutaneously (Simpkins, J. W., et al., *J. Pharmacol Exp. Ther.* 244:195 (1988)).

A drug traditionally used in the treatment of inflammatory bowel disease is sulfasalazine. Sulfasalazine is composed of the antibacterial sulfapyridine linked to the anti-inflammatory 5-ASA with an azo bond. When the drug was first introduced in 1941, the sulfa moiety was regarded as the major therapeutic determinant in the action of sulfasalazine. It was later recognized that the 5-ASA is responsible for the clinical effect, while the sulfapyridine causes most of the side effects of the drug (Khan, A. K., et al., Lancet 2:892 (1977)). In fact, the sulfasalazine is a prodrug which carries the active 5-ASA to the colon, where bacterial azo reduction releases the molecule with the desired therapeutic properties (Klotz, U., *Clin. Pharmacokin* 10:285 (1985)).

Based on the understanding of the mode of action of sulfasalazine, a second generation of the sulfasalazine has been developed: azodisalicylate and salicylazobenzoic acid. Azodisalicylate is composed of two 5-ASA molecules in which the amino groups of the two molecules are linked through an azo group. When it is reduced by colonic bacteria, the azodisalicylate delivers twice the amount of 5-ASA, and avoids the undesired action of the sulfapyridine (Willoughby, C. P., et al., *Gut* 23:1081 (1982); Bartalsky, A., *Lancet* 1:960 (1982)).

The 5-ASA prodrugs, including sulfasalazine, azodisalicylate and salicylazobenzoic acid, represent a slightly different approach from the classic prodrug delivery concept in that release of the parent drug is mediated by bacterial enzymes located at the target organ, rather than by enzymes of the target tissues. The realization that enzymes characteristic of inhabitant microorganisms of the colon may convert prodrugs and other molecules to active therapeutics led to an increase in research activity in the area of microbially controlled drug delivery to the colon.

A modified method to deliver 5-ASA to the colon was reported by Brown, Parkinson and co-workers who, in order to eliminate the effects of the sulfapyridine fraction, azo-linked sulfasalazine to a high molecular weight polymeric backbone. The resulting water-soluble polymer was shown to release 5-ASA in the presence of anaerobic rat cecal bacterial.

Pharmacokinetic analysis of 5-ASA levels following the polymeric prodrug administration showed similar deliveries of 5-ASA and metabolites to the lower bowel, blood, and urine of orally dosed rats. Pharmacodynamic analysis showed that the polymer also decreased the carrageenan-induced ulcerative-colitis-like inflammatory response in guinea pigs, based on quantitative histopathological results. This pharmacodynamic response was found to be equal to the one achieved after direct administration of 5-ASA and superior to sulfasalazine (Brown, J. P., et al, *J. Med. Chem.* 26:1300 (1983)).

Friend and Chang glycosylated selected steroid drugs commonly used in the treatment of inflammatory bowel disease (hydrocortisone, prednisolone, dexamethasone, and fluorocortisone). Glycosylation was accomplished using galactose, glucose, and cellobiose which are known to serve as substrates for colonic bacteria (Cummings, J. H., et al., *Amer. J. Clin. Nutr.* 45:1243 (1987)). The glycoside prodrugs were incubated with homogenates of the contents of various regions of the rat alimentary canal. In the stomach, proximal ileum, and distal ileum, it was found that the rate of hydrolysis of all prodrugs was relatively slow. However, the rate of hydrolysis was higher in homogenates of the contents of the cecum.

The authors concluded that delivery of glycoside prodrugs to the colon depends upon the different rates of hydrolysis in the various segments of the alimentary canal, the different transit times in those segments, and the octanol/water partition coefficient of the prodrugs. Thus, the faster transit in the upper GI tract coupled with its slow observed degradation activity, and the slow transit in the cecum, in which relatively faster degradation occurs, suggest the potential use of glycoside prodrugs to treat large bowel disease (Friend, D. R., et al., *J. Med. Chem.* 28:51 (1985)).

The covalent functionality of azoaromatic compounds, susceptible to cleavage by the colonic bacteria, was recently utilized by Saffran and co-workers (Saffran, M., et al., *Science* 233:1081 (1986); Saffran, M., et al., *J. Pharm. Sci.* 77:33 (1988)). Assuming that the distal part of the small bowel and the colon are the preferred sites for intestinal absorption of protein drugs, insulin and lysine-vasopressin solid dosage forms (pellets and gelatin minicapsules) were coated with copolymers of styrene and hydroxyethyl-methacrylate cross-linked with divinylazobenzene.

It was postulated that this polymer is able to protect the entrapped protein drugs against the digestive enzymes of the stomach and the upper portion of the small intestine, and that the polymer is degraded upon arrival at the colon. Indeed, when incubated in fecal content of rat or human for eight days, perforation of the polymer coat was microscopically detected. In addition, sustained pharmacological response of the protein drugs, antitiuresis for lysine-vasopressin, and hypoglycemia for insulin, was observed when the coated delivery systems were orally administered to rats, and later to dogs (Saffran, M., et al., *Diabetes* 38S:81A (1989)).

A delivery system of antiamoebic drug, relying on specific phagocytosis of the carrier by *Entamoeba histolytica*, which is confined to the lumen of the large intestine, has been reported (Mirelman, D., et al., *J. Infect. Dis.* 159(2):303 (1989)). Small silica particles covalently linked to nitroimidazole-based drug were designed to eliminate the parasite from the lumen of diseased humans. It was found that *E. histolytica* trophozoites avidly phagocytosed the tiny particles and released the bound drug, causing rapid cell death of the trophozoites both in vitro, and in vivo in hamsters. Although the amount of digested particles did not exceed 5% of the total number of particles, it was stated that this was enough to cause the death of most of the trophozoites population in 24 hours. In the absence of amoebic trophozoites, no significant release of the covalently bound drug was observed.

While there is evidence that certain proteins and peptides such as interleukin-II, interferon, colony-stimulating factor, tumor necrosis factor, and melanocyte-stimulating hormone may create new and effective therapies for diseases that are now poorly controlled, the acceptance of these proteins as drugs is currently limited by the methods of delivery. Colonic delivery may be a preferred route of administration for these and other new protein and peptide drugs.

Colonic delivery is also important for targeting drugs to the colon, particularly for the treatment of inflammatory bowel disease (IBD) and ulcerative colitis. However, the currently available enterally administered preparations of drugs designed for colonic delivery are not feasible for long-term use in humans, in part because of the potential toxicity of the azo compounds. These exists a need for an improved colonic delivery system that can be used with a wide variety of drugs and bioactive compounds.

SUMMARY OF THE INVENTION

The invention is directed to a colonic delivery system comprising a drug, in combination with a matrix, such matrix comprising a saccharide-containing polymer, and such matrix being resistant to chemical and enzymatic degradation in the stomach and small intestine of the subject who is administered the colonic delivery system.

The colonic delivery system of the invention further provides a method for enterally administering a drug or other bioactive compound to a patient in need of such drug whenever it is necessary that such drug escape gastrointestinal digestion.

The colonic delivery system of the invention further provides a method for delivering efficacious levels of drugs designed for the treatment of diseases of the colon to the colon.

The invention further provides methods for the preparation of oligosaccharide-containing polymers, suitable as matrices for the drug delivery systems of the invention. More particularly, the invention provides methods of modifying natural polymers, such as mucopolysaccharides and particularly chondroitin and pectin, to be suitable as matrices for the drug delivery system of the invention.

DETAILED DESCRIPTION OF THE PREFERRED EMBODIMENTS

Definitions

Figure 1:
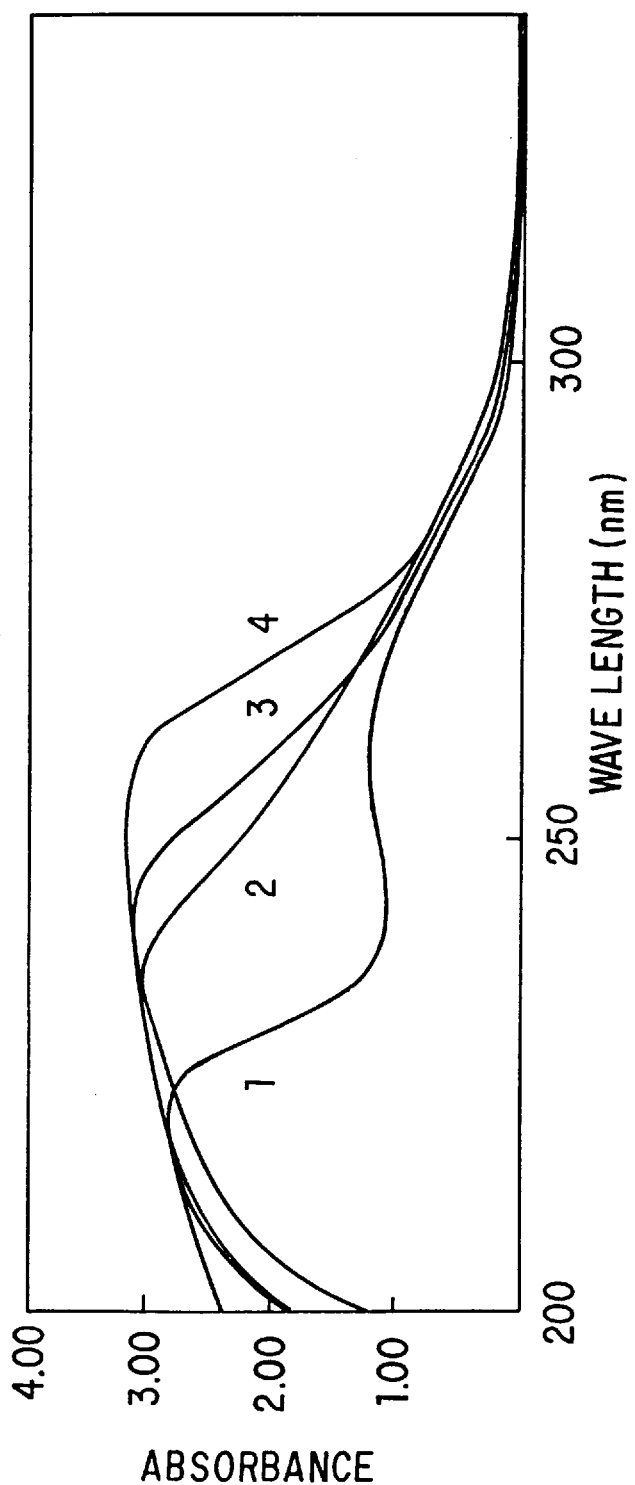
FIG. 1. Typical U.V. spectrum of chondroitin and modified chondroitin products in hydroalcoholic solutions. 1: chondroitin, 2: RMN 70; 3: RMN 60; 4; RMN 55.

In the description that follows, a number of terms used in pharmacology are extensively utilized. In order to provide a clear and consistent understanding of the specification and claims, and the scope to be given such terms, the following definitions are provided.

By the term "colon" is meant that part of the large intestine that extends from the cecum to the rectum. The cecum is the blind pouch in which the large intestine begins and into which the ileum opens from one side.

By the term "matrix" is meant a material comprising a saccharide-containing polymer, wherein the saccharide-containing polymer is preferentially degradable in the colon.

By being "preferentially degradable in the colon" is meant that the substance, when taken orally by a subject, (1) is relatively resistant to chemical and enzymatic degradation in the stomach and small intestine of such subject, and (2) is relatively susceptible to degradation in the colon so as to be capable of providing or otherwise releasing efficacious levels of a desired drug(s) in the colon of such subject.

By the term "saccharide-containing polymer" is intended polymeric constructs comprising a synthetic oligosaccharide-containing biopolymer or saccharide-containing natural polymers. Examples of synthetic oligosaccharide-containing polymers useful in the compositions and methods of the invention include methacrylic polymers covalently coupled to oligosaccharides such as cellobiose, lactulose, raffinose, and stachyose. Examples of saccharide-containing natural polymers useful in the methods of the invention include modified mucopolysaccharides such as cross-linked chondroitin sulfate and metal pectin salts, for example calcium pectate.

By the term "drug" is meant any pharmaceutical or physiological agent, composition, bioactive compound, or combinations thereof, useful in the diagnosis, cure, mitigation, treatment, or prevention of a disease, or for any other medical purpose. The term "drug" is intended to be interpreted broadly and is not limited in terms of chemical composition or biological activity.

The invention is directed to a colonic delivery system comprising a drug in combination with a matrix, said matrix comprising a saccharide-containing polymer. The colonic delivery system of the invention is based upon the ability of the colonic bacteria to digest substances that are not degraded in the stomach or the small intestine, or are degraded to only a minor extent.

The colonic delivery system of the invention serves as a means to target enterally administered drugs to the large intestine. When the drug-matrix composition of the invention is present in the stomach or the small intestine, its drug content is shielded by the matrix and is not affected by enzymes or pH of these organs. After the drug-matrix composition reaches the colon, bacterial enzymes degrade the matrix, thereby releasing the drug.

Accordingly, a subject in need of treatment with a desired drug, especially when it is desired to target the desired drug to the site of such subject's colon, may conveniently obtain such treatment by orally ingesting the composition of the invention. Alternatively, if desired, the composition of the invention may be provided in suppository form. Examples of drugs that may be provided in the composition, delivery system and methods of the invention include, for example, peptide and protein drugs such as analgesics, oral vaccines, plasminogen-activating peptides, contraceptive peptides, growth-promoting peptides, steroid drugs, such as dexamethasone, budesonide, beclomethasone, flucticasone, tioxocortol and hydrocortisone, protein drugs that may survive longer and be absorbed better from the colon than from the small intestine, such as LH/RH and insulin, drugs which have been proved to possess colonic absorption such as theophylline, isosorbide dinitrate, nifedipine, oxprenolol, antispasmodic agents for the treatment of Irritable Bowel Syndrome such as cimetropium bromide, anti-neoplastic agents such as methotrexate, tamoxifen, cyclophosphamidle, mercaptopurine and etoposide, other drugs such as cyclosporin, and monoclonal antibody-containing preparations. In addition, chemotherapeutic agents useful in the treatment or mitigation of colon tumors may be provided.

The therapeutic benefits of the colonic delivery system depend upon its ability to directly deliver efficacious levels of drugs to the colon. This allows the local treatment of colonic diseases, such as ulcerative colitis or colon carcinoma. Direct delivery of drugs to the colon enhances the amount of drug absorbed in the colon, and the amount of drug to which colon cells are directly exposed. Direct delivery or targeting of drugs also decreases the systemic distribution of the drugs, thereby reducing undesirable and potentially harmful side effects. Additionally, some drugs are known to be more efficiently absorbed in the large intestine than in other portions of the GI tract. These include, for example steroids, xanthines and others. Direct delivery of such drugs to the large intestine would considerably decrease the required effective dose.

In the controlled-release systems currently known in the art, drugs are released by diffusion mechanisms during transit of the drug-containing composition through the gastrointestinal tract. Once the drug reaches the lower portion of the gut, the release process became limited due to low fluid content and high viscosity in this portion of the GI tract. This decrease in release rate leads to a decrease in drug absorption.

According to the present invention, however, these and other problems of current drug delivery methods are overcome by incorporating some of the drug into a suitable matrix (e.g., in a tablet core) which undergoes bacterial degradation in the colonic surroundings and releases its drug content at least at efficacious levels, leading to improved bioavailability of the drug.

The flora typically found in the human gastrointestinal tract is summarized in Table 1. The flora may change depending upon the physiological condition of the person or animal being treated. Drug delivery may be designed to specifically target a type of flora known to be in abundance in the patient.

TABLE 1

The Human Gastrointestinal Flora

| | Stomach | Jejunum | Ileum | Feces |
|---|---|---|---|---|
| Total bacteria count | $0–10^3$ | $0–10^5$ | $10^3–10^7$ | $10^2–10^{12}$ |
| Aerobic or Facultative Anaerobic Bacteria | | | | |
| Enterobacteria | $0–10^2$ | $0–10^3$ | $10^2–10^6$ | $10^4–10^{10}$ |
| Streptococci | $0–10^3$ | $0–10^4$ | $10^2–10^6$ | $10^5–10^{10}$ |
| Staphylococci | $0–10^2$ | $0–10^3$ | $10^2–10^5$ | $10^4–10^7$ |
| Lactobacilli | $0–10^3$ | $0–10^4$ | $10^2–10^5$ | $10^6–10^{10}$ |
| Fungi | $0–10^2$ | $0–10^2$ | $10^2–10^3$ | $10^2–10^6$ |
| Anaerobic bacteria | | | | |
| Bacteroides | Rare | $0–10^2$ | $10^3–10^7$ | $10^{10}–10^{12}$ |
| Bifidobacteria | Rare | $0–10^3$ | $10^3–10^5$ | $10^8–10^{12}$ |
| Gram-positive cocci$^a$ | Rare | $0–10^3$ | $10^2–10^5$ | $10^8–10^{11}$ |
| Clostridia | Rare | Rare | $10^2–10^4$ | $10^6–10^{11}$ |
| Eubacteria | Rare | Rare | Rare | $10^9–10^{12}$ |

$^a$Includes Peptostreptococcus and Peptococcus.
(from Simon, G.L., et al., Gastroenterology 86:174 (1984))

In one preferred embodiment, methacrylic polymers are employed because of their chemical stability in a biological environment. In particular, the polymers are not catabolized and absorbed in the gastrointestinal tract. These polymers do not contain extractable irritating compounds and have been demonstrated to be useful in, for example, surgical, ophthalmological, and dermatological applications.

The oligosaccharides that are covalently bonded to the acrylic polymers are preferably those which can be digested by colonic bacteria but not by the enzymes of the stomach or the small intestine. Examples of such oligosaccharides are cellobiose (4-O-β-D-glucopyranosyl-D-glucopyranose), lactulose (4-O-β-D-galactopyranosyl-D-fructo-uranose), the trisaccharide raffinose(α-D-Gal-[1→6]-α-D-glc-β-D-fru), and stachyose(α-D-Gal-β-2-D-Gal-β-D-Glc-β-D-Fru).

Several methods of coupling the oligosaccharides to the acrylic monomer can be used, some of which are direct and others of which involve at least two steps.

In an example of a direct method, esters of methacrylic acid with sugar alcohols can be prepared by the trans-esterification of methyl methacrylate or by acylation with methacryloyl chloride.

Theoretically, numerous hydroxyl groups in oligosaccharides can react. However, the monosubstitution of the methacrylic acid is primarily in the 6 position (the primary alcohol). By using an excess of methacryloyl chloride or methyl methacrylate relative to the oligosaccharide used, a diester is produced which is useful as a cross-linking unit in the polymerization process.

In one example of a two-step method, a reactive group is introduced at a specific site on the oligosaccharide. A preferred embodiment, which does not require protection of the hydroxide groups, is reductive amination at the reducing end of the oligosaccharide, to form the acrylic 1-amino-1-deoxy-alditol. In the reductive amination step, ammonia may be used. Alternatively, a suitable diamine may be used. One amino group of the diamine binds to the sugar, leaving the second amino group available for the second step reaction with the acrylic monomer.

The amination can be performed using reactants such as ammonium bicarbonate, ammonium acetate, ethylene diamine or 2-(4-aminophenol)-ethylamine. The reduction of the amino sugar can be performed with sodium borohydride, sodium cyanoborohydride, hydrogen gas with platinum oxide, paladium (10% Pd/C) or Raney Nickel.

After the amination of cellobiose, the glycosylamine produced is combined with methacryloyl chloride or with methacrylic acid to produce the methacrylic monomer.

Polymerization is carried out to produce homopolymers of the previously synthesized monomer-oligosaccharides, or preferably to produce copolymers with monomers such as acrylate methacrylate, hydroxypropyl-methacrylate or hydroxyethyl-methacrylate.

Natural polymers such as mucopolysaccharides can also be degraded by colonic bacteria. The enzymes responsible for the bacterial catabolism of these polymers vary from polymer to polymer, and they can be either cell-associated or extra-cellular enzymes.

However, most of these natural polymers are, in their unmodified form, soluble in water and gastric fluid, and thus are not suitable as carriers for colonic drugs without modification. For example, chondroitin sulfate, which is a mucopolysaccharide, is a very soluble polymer and as a solid dosage form disintegrates quickly in water. Chondroitin sulfate has been reported as a substrate for the bacteroid inhabitants of the large intestine, mainly *B. thetaiotamicron and B. ovatus* (Salyers, A. A., *Amer. J. Cli. Nutr.* 13:158–163 (1979); Salyers, A. A. and O'Brien, M., *J. Bacteriol.* 143:772–780 (1980)). It was suggested that periplasmic enzymes are responsible for the breakdown of chondroitin, probably by an outer membrane receptor which binds chondroitin sulfate and brings it into contact with enzymes such as chondroitin-sulfate lyase.

Cross-linking methods may be used to reduce the hydrophilicity of these polymers and thus allow their utility in the compositions and methods of the invention as colonic drug carriers which pass the small intestine and degrade in the colon. An example of a preferred cross-linking method is amide protection by the reaction of diamine with the polymer. Diamines that can be used include: 1,4 butanediamine, 1,6 hexanediamine, 1,7 heptanediamine and 1,12 dodecanediamine.

Thus, the invention provides a method of modifying chondroitin sulfate wherein chondroitin sulfate is bought into contact with a diamine compound selected from the group consisting of 1,4-butanediamine, 1,6-hexanediamine, 1,7-heptanediamine and 1,12-dodecanediamine, in a suitable medium in the presence of a suitable catalyst, for a suitable period of time, the product is dialyzed in water and then lyophilized. 1,12-dodecanediamine is a preferred amine. Said medium is preferably dimethylsulfoxide or dimethylformamide. The catalyst is preferably dicyclohexylcarbodiimide.

The invention also provides a method of modifying pectin, wherein an aqueous solution of pectin is mixed with a metal chloride solution in which the concentration of the salt is adjusted to the desired degree of solubility of the final product using methods known in the art, the pH of the mixture is adjusted to 8–8.5 with sodium hydroxide to form a gel, followed by a precipitate, which is centrifuged and rinsed with water. The solid metal salt of pectin is obtained, which is sieved to give a powder. Suitable metals salt of pectin include, for example, the calcium, strontium, and magnesium salt, with calcium being preferred.

After preparing the oligosaccharide-polymer matrix, the matrix is combined with a drug. Methods are known for formulating a composition to allow controlled release of the chosen pharmaceutical compound. Using these and other known methods, compositions of the desired pharmaceutical compound may be formulated with the polymers of the present invention. Examples of such methods are disclosed in Saffran et al., *Science* 233:1081–1084 (1986) and Levine et al., *Gastroenterology* 92:1037–1044 (1987).

Specific embodiments of prepared formulations of the compositions of the invention, include, for example, matrix-drug tablets, especially tablets prepared by compression; matrix-drug pellets, either free or packed in gelatine capsules, or any other means allowing oral administration; matrix-drug nanoparticles, either free or packed in gelatine capsules or any other means allowing oral administration; and multi-layered tablets which comprise cored drug, coated with biodegradable polymers, the polymeric layer being prepared, for example, by spray-coating, molding or double-press procedure. All of these techniques for preparation of such formulations are well known in the art.

The amount of drug can vary as desired for efficacious delivery of the desired drug and in consideration of the patient's age, sex, physical condition, disease, and other medical criteria. In addition, the amount of drug delivered by the system of the invention will depend upon the relative efficacy of the drug. The amount of specific drug necessary for efficacious results in the delivery system and methods of the invention may be determined according to techniques known in the art. For example, recommended dosages such as known in the art (or example, see the *Physicians' Desk Reference*, 1991 (E. R. Barnhart, publisher), *The Merck Index*, 10th Edition, Merck & Co., New Jersey, and *The Pharmacological Basis of Therapeutics*, 8th edition, A. G. Goodman et al., eds., Pergamon Press, New York), provide a basis upon which to estimate the amount of a drug which has been previously been required to provide an efficacious level of activity. Especially, amounts of a desired drug that have previously been administered by suppository formulations, and the known characteristics of such drug when administered by suppository, are useful in this regard. Since the delivery system of the invention does not depend upon systemic (blood) delivery of the drug to the colon, it may be expected that efficacious levels of colon drugs that must be administered to a patient systemically will be higher than efficacious levels of such drugs when delivered directly to the colon.

Examples of drugs whose efficacious amounts for use in the delivery system of the invention may be determined in this manner include anti-inflammatory agents including non-steroidal and steroidal anti-inflammatory agents, dexamethasone, budesonide, beclomethasone, flucticasone, tioxocortal, and hydrocortisone, cyclosporin, theophylline, nifedipine, isosorbide dinitrate, oxyprenolol, cimetropium bromide, anti-neoplastic agents including methotrexate, tamoxifen, cyclophosphamidle, mercaptopurine etoposide, and indomethacin.

Tablets and capsules may be prepared and tested by techniques well known in the art, for example, as described in *Remington's Pharmaceutical Sciences*, Mack Publishing Company, 16th edition, 1980, and especially in chapter 89, the pharmaceutical preparation and manufacture of "Tablets, Capsules and Pills." In all embodiments, if desired, more than one drug may be supplied to the patient in the same matrix.

In the tablet embodiments, for example, the compositions of the invention may provide a wide range of drug amounts, for example, the amount of drug can vary from about 5 to 30% by weight.

In another embodiment, a compressed tablet is formulated to contain efficacious levels of the desired drug(s) or pharmaceutical compound(s) as in the tablet embodiment, and an amount of the polymer of the invention that would allow disintegration of the tablet and release of the drug(s) following exposure of the tablet to one or more microorganisms present in the colon.

Other suitable embodiments will be known to those of skill in the art. A useful formulation will be suitable for enteric administration, will contain a drug targeted for release in the colon, and will further comprise an oligosaccharide-polymer matrix according to the invention. The formulation will be designed so as to allow protection of the drug from stomach and intestinal enzymes, but permitting degradation of the oligosaccharide-containing matrix and release of the drug upon exposure of the formulation to colonic bacteria.

The delivery system and methods of the invention not limited to administration to humans and are especially useful for veterinary administration of drugs to any animal, including pets such as dogs, cats horses, fish and birds, zoo animals, wild animal control and treatment, and agriculturally important animals of the food and dairy industry such as cattle, milk cows, swine and poultry.

The following examples further describe the materials and methods used in carrying out the invention. The examples are not intended to limit the invention in any manner.

EXAMPLE 1

Formation of Acrylic Oligosaccharide Monomers by One-Step Method

A. Trans-esterification

Two mmole raffinose was mixed with 6 mmole methyl methacrylate in 15 ml of dimethylformamide in the presence of 20 mg of 4-ethoxyphenol (MEHQ) and 10 mmole of sodium carbonate. The reaction mixture was heated to 70°–75° C. under vacuum of 100 mm Hg. A seven-plate fractionating column was installed for stripping the methanol from the system. After 12 hours the mixture was cooled. The product was identified using a TLC plate and further eluted from silica gel 60 column with ethylacetate.

B. Acylation

Two mmole raffinose was mixed with 6 mmole methacryloyl chloride, 10 mmole sodium carbonate (dried) and 20 mg of 4-ethoxyphenol in 15 ml dimethylformamide or dimethyl sulfoxide. The mixture was heated to 80° C. for 7 hours under vacuum (100 mm Hg). Identification and purification were performed as in Example 1A.

EXAMPLE 2

Formation of Acrylic Oligosaccharide Monomers by Two-Step Method

A. Three mmole of cellobiose and 3 mmole of sodium cyano-borohydride were mixed with 5 ml ethylenediamine (75 mmole) in a 25 ml flask at 5°–10° C. (ice bath). The reaction process was followed up using TLC plates and developing system of butanol-ethanol-water (5:3:2). The products were identified with iodine or ninhydrine spray.

B. 0.3 mmole of cellobiose was dissolved in 8 ml water, then 11 mmole sodium cyanoborohydride and 7.2 mmole ammonium acetate was added and mixed together in an ice bath. The same follow-up as in Example 1 was performed.

C. 3 mmole of cellobiose was dissolved in 33 ml of water, then 9 mmole of sodium cyanoborohydride was added and the mixture was cooled to 10° C. in an ice bath. 60 mmole ammonium bicarbonate was added and the reaction was continued for 8 hours at 10° C. and then for 64 hours at room temperature. Follow-up of the reaction process was performed by TLC as in Example 3, but with phenol sulfuric acid assay for identification. After 8 hours the mixture was evaporated to dryness, then 10 ml water was added and the mixture was again dried. Separation and isolation of the product was carried out in an Amberlite IR-120 (H) column (23 cm×2 cm I.D.). The mixture (15 ml) was acidified to pH 5.5 with acetic acid, then 85 ml of water were added and the mixture was passed through the column (1.5 ml/min). The column was washed with 250 ml water then with 250 ml ammonia (0.7M) and again with 250 ml water. The ammonia and the water fractions were collected and evaporated to dryness.

EXAMPLE 3

Linkage to Acrylic Monomer

A. Schotten-Baumann Reaction

Three mmole of the product of Example 2C was dissolved in 2 ml water and the solution was cooled in an ice bath to 2°–4° C. Three mmole of NaOH was added to the solution. On cooling 3 mmole of methacryloyl chloride and an additional 3 mmole of NaOH in 2 ml of water were added dropwise and simultaneously. The reaction mixture was stirred at room temperature for an additional hour. Followup of the reaction was performed by TLC (silica gel plates, BuOH/EtOH/$H_2O$ at a ratio of 5:3:2).

B. Three mmole of the product of Example 2C was stirred with 3 mmole of methacrylic acid in 5 ml dimethylsulfoxide. 3.3 mmole of dicyclohexylcarbodiimide (DCC) was added to the reaction mixture and this was stirred for 24 hours at room temperature.

EXAMPLE 4

Polymerization

Raffinose-cross-linked methacrylic copolymer 10 mmoles of the product of Example 1 were taken with 20 mmoles of methacrylic acid in acetone or tetrahydrofuran (3 ml). 45 mg of aso-bis-isobutyronitrile as initiator was added and the polymerization was carried out at 55° C. under a nitrogen atmosphere.

After 24 hours, 5 ml of water were added to the mixture and the solvent was evaporated by reduced pressure for 1 hour. The mixture was then transferred to a dialysis bag and dialyzed in 10 liters of distilled water for 24 hours. The end product was then taken out and lyophilized.

EXAMPLE 5

Modification of Natural Polymers

A. Modification of Chondroitin

1. One g of chondroitin sulfate was taken with 11 mmole, 1,12 dodecandediamine and 24.2 mmole dicyclohexylcarbodiimide in 10 ml of dimethylsufoxide or dimethylformamide. The reaction was carried out at room temperature for 12 hours. The reaction mixture was then placed in a dialysis bag and dialyzed in 3 liters of distilled water for 48 hours. The purified material was lyophilized.

2. Chondroitin sulfate type A (Sigma, St. Louis, Mo.) was treated with 1–12 diaminododecane (Sigma, St. Louis, Mo.) in equimolar ratios of 30%, 50% and 60%. The purification procedure of the polymer included rinsing with acetone and dialysis in purified water. The obtained product as then freeze-dried overnight and the resulting dry powder was collected and sealed until further processing.

The batch to bath uniformity of the products was ascertained by scanning their absorbance spectra in 1% w/v hydroalcoholic (1 part water, 2 parts ethanol) solution (FIG. 1). The degree of treatment was determined by measuring the amount of methylene blue which was adsorbed on the various products. Chondroitin sulfate and the treated chondroitin products were mounted in a dialysis bag [Spectra/por 6×30 mm, m.w. cut off 12,000–14,000 daltons (Spectrum, LA)] and immersed in 0.1% w/v methylene blue in veronal buffer. The methylene blue in turn, diffused into the bag and adsorbed onto the dispersed carrier powder. The chromophor disappearance during 6 hours was monitored in a spectrophotometer (Spectronic 1001, Milton Roy) at 665 nm. The absorbance at equilibrium was taken and divided by the value obtained when chondroitin sulfate was mounted in the dialysis bag. The yield value multiplied by 100 was determined as a Relative Methylene Blue Adsorption Number (RMN). Thus the value of the 30% treated chondroitin was found to be 68.6, the value for the 50% treated chondroitin was found to be 60.5. and the value for 60% treated chondroitin was 54.4. The respective RMN (rounded to the nearest decimal value) was 70, 60, and 55 respectively.

B. Modification of pectin

5% w/v pectin aqueous solution is mixed with 70% w/v $CaCl_2$ at a ratio of 1:1. The pH of the obtained opalescent solution is 2–2.5. The pH is than adjusted to a value of 8–8.5 by gradual addition of 1N NaOH. A gel is formed, followed by a precipitate, which is centrifuged at 5000 rpm and rinsed with purified water. This procedure is repeated three times, The obtained slurry is than dried in a shelves oven for 48 hours, to a final water content of 5%. The solid calcium pectate is comminuted and passed through a 40 mesh sieve, to give a powder.

Calcium chloride solutions of 50, 60, 80 and 90% w/v can also be used to produce more soluble (50, 60%) or less soluble (80 and 90%) products.

Other divalent cations, such as magnesium ($Mg^{++}$), or strontium ($Sr^{++}$), can be used for the same purpose of preparing pectic salts suitable as matrices for colonic delivery systems.

EXAMPLE 6

A. In Vitro Studies with Modified Chondroitin

1. Chondroitin sulfate is a soluble mucopolysaccharide which can be utilized as a substrate by the bacteria of the large intestine. A solid delivery system useful in the methods of the invention was prepared from cross-linked chondroitin sulfate, as obtained in Example 5(A)(1), in the form of a compressed tablet in combination with indomethacin. Drug release was tested using rat cecal homogenate at 37° C.

The release rate of indomethacin from a cross-linked chondroitin was lower than that of the plain chondroitin used as a control. When examined in the presence of cecal homogenate, 54% of the drug was released from the untreated carrier within 60 minutes, whereas only 17.6% was released from the treated carrier. Comparable studies using a medium not containing the homogenate, showed a different release profile. When the treated chondroitin was examined, 32.5% of indomethacin was released after 60 minutes in a buffer (compared to 17.6% released in the cecal homogenate). In a parallel experiment, 67.8% of indomethacin was released from non-treated chondroitin in the same buffer (compared to 54% released in the presence of a cecal homogenate).

2. The modified chondroitin dry powder obtained in example 5(A)(2) was sieved, and mixed with indomethacin (Sigma) at a ratio of 9:1 w/w. Matrices, each weighing 200 mg were than compressed, using a Perkin Elmer manual press.

Cecal content medium—Sabra rats (I. Lutsky, F. Aizer, and N. Mar. Is. J. Med. Sci. 20:603–612, 1984), weighing 200–300 g., were fed with chondroitin sulphate (20% aqueous solution) 24 hours prior to the dissolution experiments. Thirty minutes before the dissolution experiments the rats were sacrificed, their cecal contents were pooled under $CO_2$ atmosphere and suspended in phosphate-buffered saline (PBS, pH 7) to give a final cecal dilution of 1.25% w/v.

Drug release experiments—The dissolution experiments were repeated three times on each formulation. Each experiment represented a different batch of the modified chondroitin and was performed in duplicate in 100 ml sealed glass vials which were shaken in water bath at 80 rpm, 37° C., under $CO_2$ atmosphere. The release experiments were performed in PBS, with or without the addition of cecal content (control). Samples (1 ml) were withdrawn in triplicate at predetermined time intervals for indomethacin assay. An equal volume of PBS was then added to the system. In a separate set of experiments, the cecal content suspension was sonicated for 3 minutes before adding the PBS. This was done to break the cecal-bacteria cell wall so that the dissolution experiment could be performed in the presence of free endo-enzymes (A. Salyers. Amer. J. Clin. Nutr. 32:158–163 (1979)). The purpose of this last preliminary study was to compare the behavior of the colonic carriers in two different enzymatic environments.

Two types of dissolution studies were performed: "short term studies" and "long term studies." The first lasted 5 hours, with sampling times of 0, 15, 30, 45, 60, 90, 120, 150, 180, 240 and 300 minutes. The short term experiments included dissolution studies in three types of media: rat cecal content, rat cecal content that were sonicated for 3 minutes ("sonicates") and control media (PBS without bacteria addition). The long-term experiments lasted 24–28 hours, with sampling times of 0, 3, 6, 9, 12, 14, 21, 24 and 28 hours. in these studies only bacteria were involved, i.e. cecal content without parallel experiments of sonicates, Indomethacin analysis Samples (1 ml) were acidified (200 $\mu$l of 0.4 N HCl) extracted with 1 ml of ethylacetate containing 0.2 mg % of flufenamic acid as internal standard. The mixture was vortexed and centrifuged (3 min at 3400 rpm). 500 $\mu$l of the organic phase was evaporated, and the residue was redissolved in phosphate buffer, pH 7.5:acetonitrile (50:50) mixture. Twenty microliters of the solution were injected into the HPLC system (Hewlett Packard 1050 pumping system, Jasco 875 Intelligent UV/v is detector, Hewlett Packard 3365 ChemStation Data analyzer and Hewlett Packard analog-digital 35900C Dual Channel Interface Convertor). The wavelength was 280 nm, and the column was 5 micron, 250×4.6 mm RP-18 (LiChroCART 250-4, E. Merck, Germany).

Statistical Analysis—The difference between the various drug amounts at different time points was analyzed for significance, using a one way paired t-test. A statistically significant difference was considered when the p value was less than 0.05.

Figure 2A:
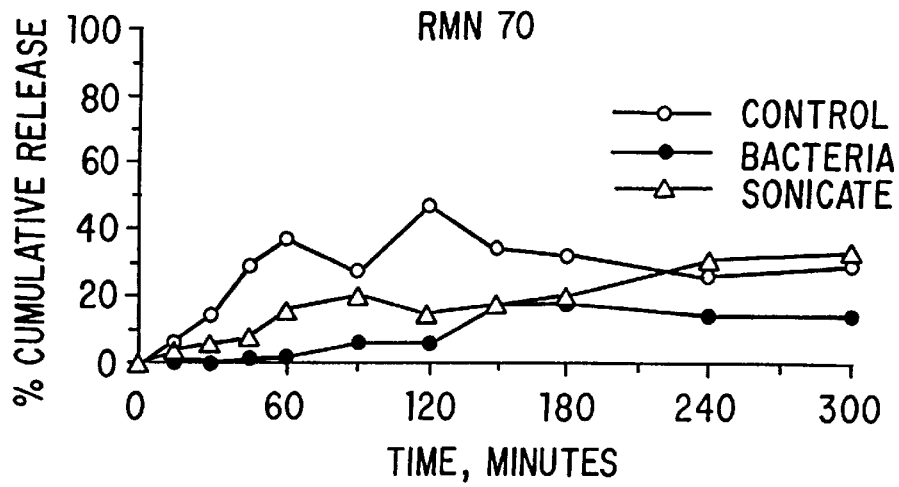
FIG. 2: Summary of "short term" (5 hours) experiments: cumulative amount of indomethacin released from three formulations, RMN 70, RMN 60 and RMN 55, in various dissolution media: (●) PBS (control), (○) rat cecal content in PBS, (Δ) sonicated rat cecal content in PBS.
Figure 2B:
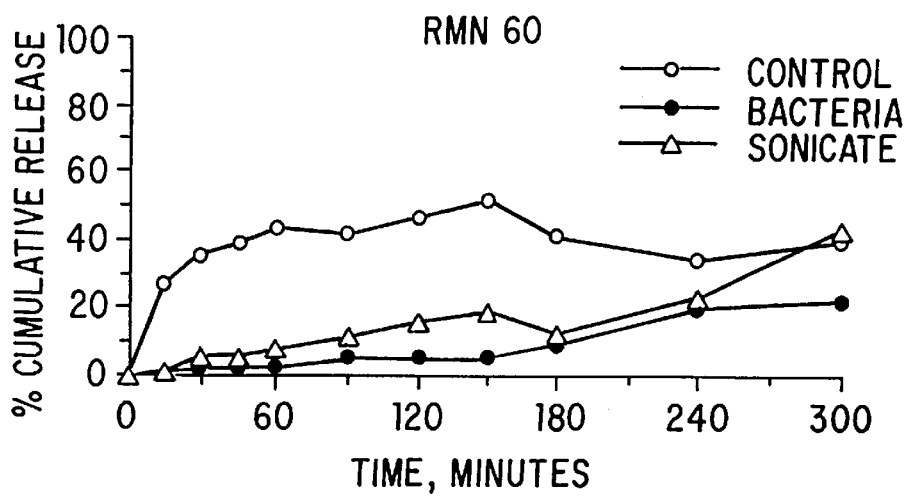
Figure 2C:
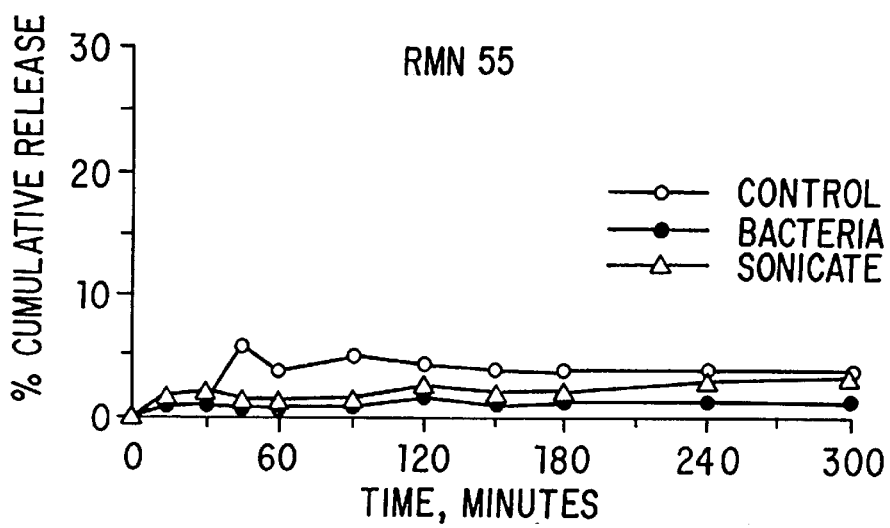

FIG. 2 summarizes the data obtained in those dissolution studies that lasted 6 hours ("short term" experiments). In all cases the amount of drug released in the control systems, i.e. without rat cecal content, was larger than the amounts that were released in the presence of cecal content or sonicated cecal contents ("sonicates"), In all cases the amount of drug which was released in the presence of the sonicates was higher than the amount in the presence of intact cecal content. However, while the indomethacin release profiles in the PBS medium reached a plateau after approximately 2 hours, the release profile of the drug in the sonicated medium slowly increased till reaching the level of the drug which was released in the control experiments (between 4 to 5 hours). The percent cumulative release of indomethacin at the end of the experiments were 29.04, 39.68 and 3.80 for RMN 70, RMN 60 and RMN 55 respectively in the PBS dissolution medium, and 32.30, 43.00, and 3.30 for RMN 70, 60 and 55 respectively in the sonicate dissolution medium. The amounts of indomethacin released in the dissolution medium that contained intact cecal medium did not reach those levels and the values obtained (in cumulative percent) were 13.80, 21.43 and 1.25 for 70, 60 and RMN 55 respectively.

Similar experiments with untreated chondroitin sulfate matrices that contained the same amount of indomethacin ended within 1 hour, at which time a total dissolution of the carrier was observed, yielding a total release of the drug. In these experiments, where untreated chondroitin served as a carrier, no significant difference was observed between the drug release profiles in the various dissolution media.

Figure 3:
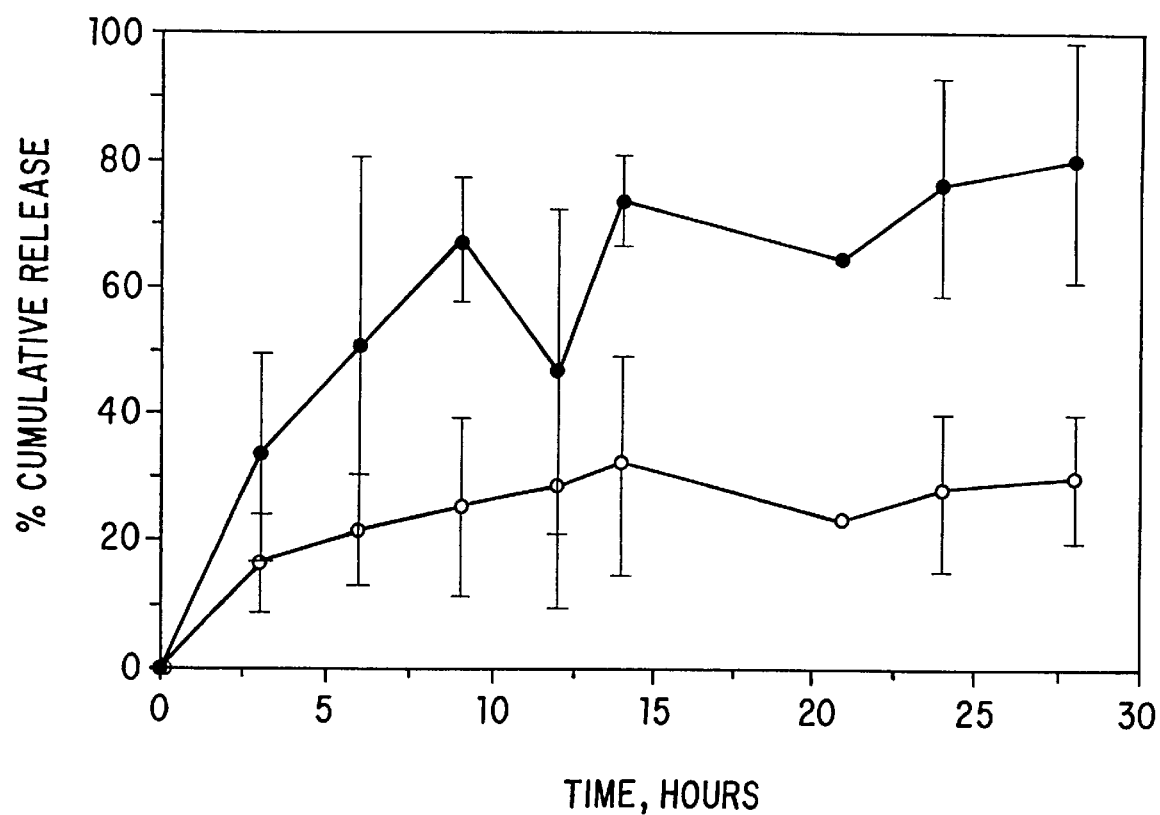
FIG. 3: Cumulative percentage of indomethacin released from RMN 70 formulation as analyzed in rat cecal content medium (●) and in PBS (○). The data are the mean of 3 sets of experiments.
Figure 4:
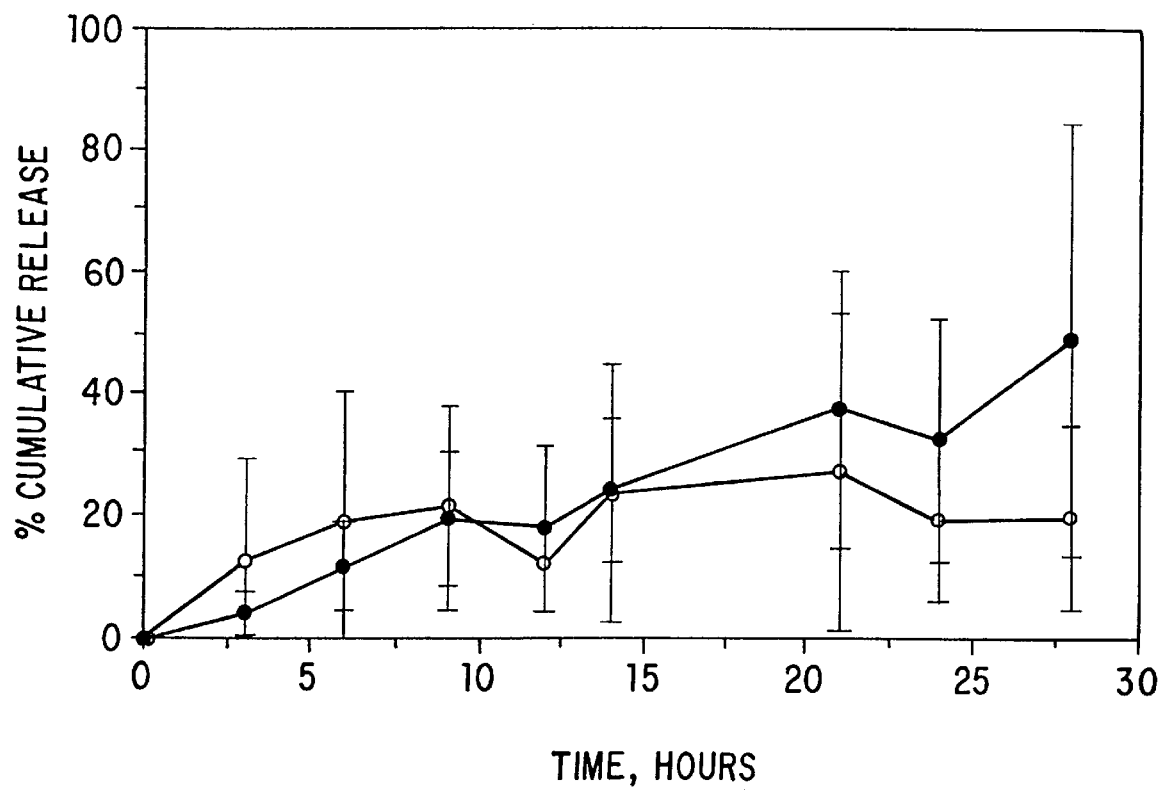
FIG. 4: Cumulative percentage of indomethacin released from RMN 60 formulation as analyzed in rat cecal content medium (●) and in PBS (○). The data are the mean of 3 sets of experiments.
Figure 5:
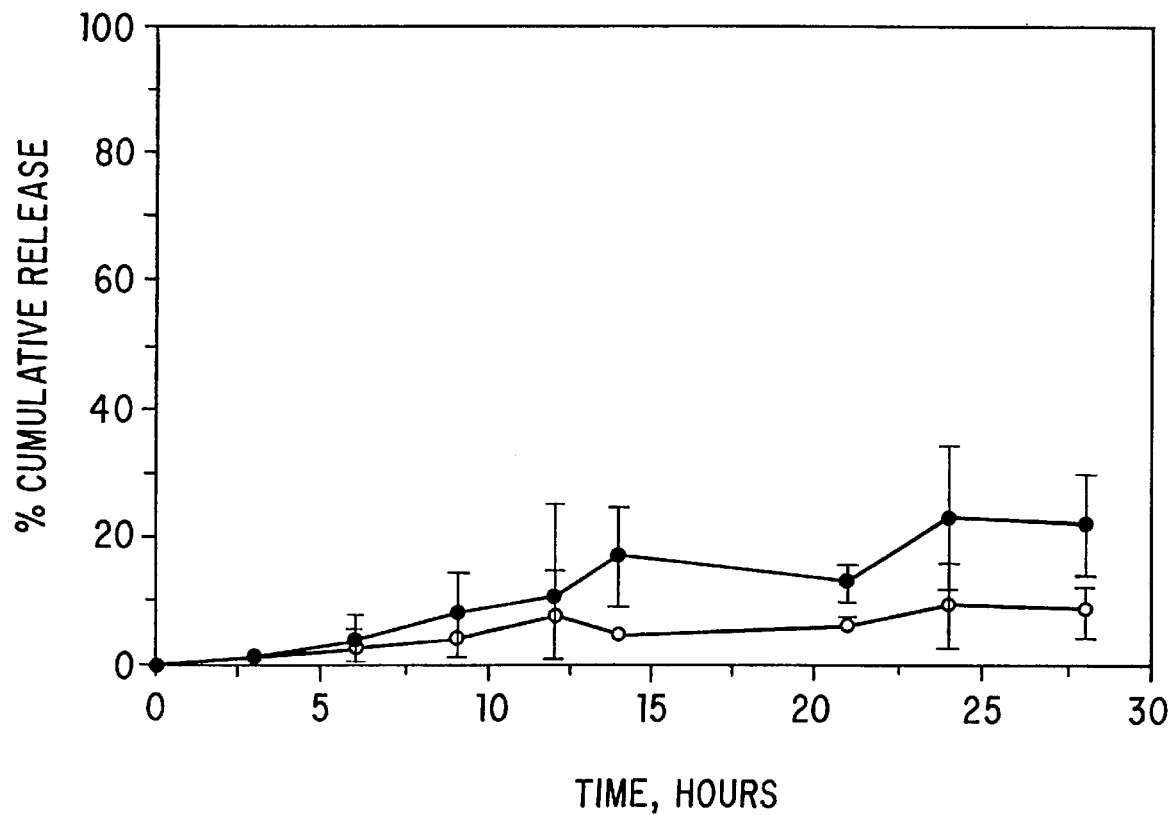
FIG. 5: Cumulative percentage of indomethacin released from RMN 55 formulation as analyzed in rat cecal content medium (●) and in PBS (○). The data are the mean of 3 sets of experiments.

Different results were achieved when the dissolution experiments were designed to last 28 hours (FIGS. 3–5). In the RMN 70 formulation the profile of indomethacin released was higher in the cecal medium than in the PBS medium along the entire experiment; and significantly ($p<0.05$) higher from 12 hours on. As for the RMN 60 formulation, after initial suppression of indomethacin release which lasted 12 hours, the release profile in the cecal content medium raised above the indomethacin profile in the PBS control. Significance in the differences as analyzed by paired t-test was achieved after 24 hours. As far as the RMN 55 formulation is concerned, the indomethacin profile in the cecal medium elevated over the profile obtained in the PBS control after 6 hours. Significant difference between the amounts of drug released in the two systems was achieved after 24 hours.

Figure 6:
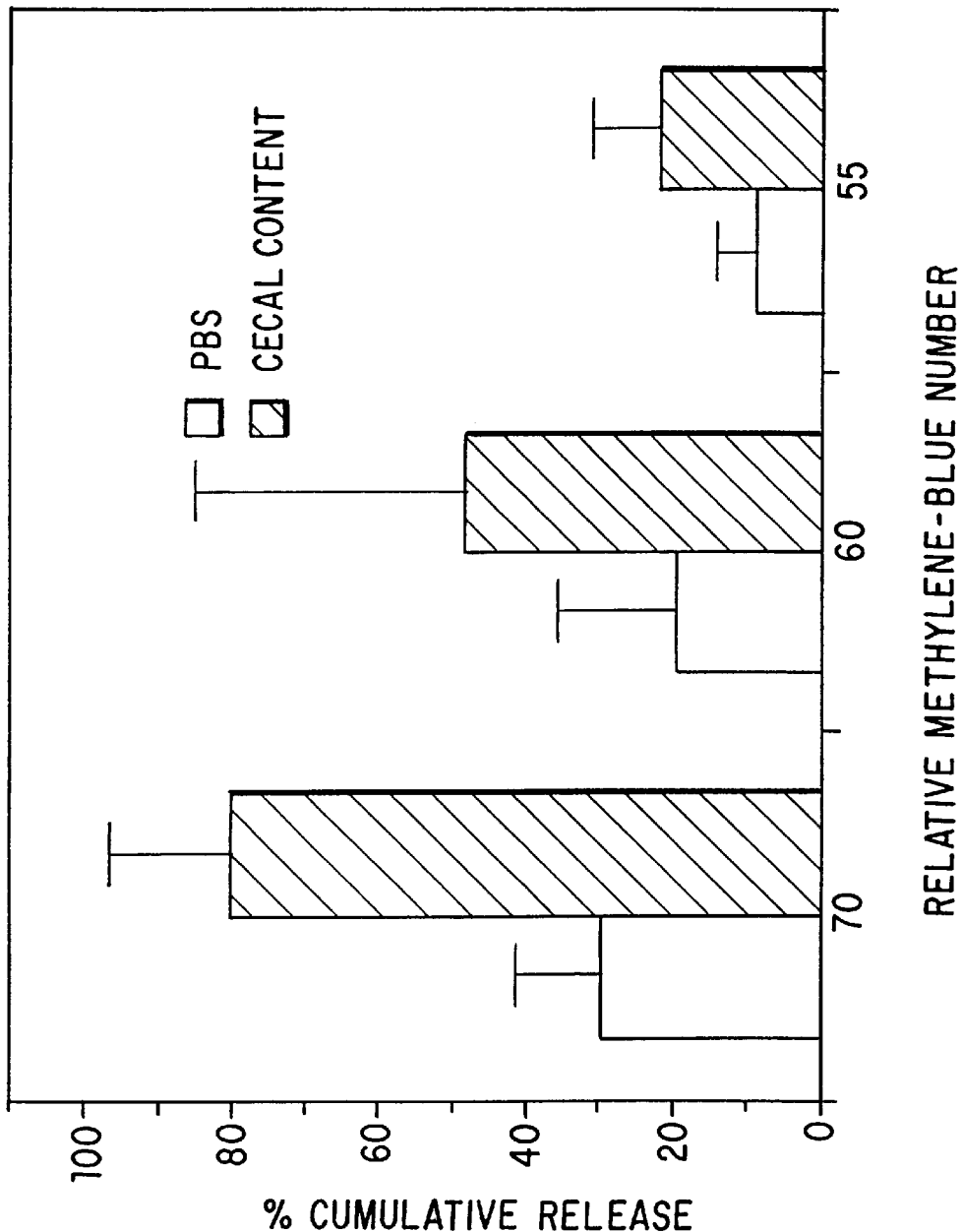
FIG. 6: Total indomethacin released after 28 hours from the three chondroitin formulations in rat cecal content and PBS control. The data are the mean of 3 different sets of experiments.

FIG. 6 shows the difference between the total amount of indomethacin released in the PBS control medium and in the rat cecal content medium at the end of the experiments (28 hours). The values for the PBS were: 30.07±10.01, 19.65±14.96, 9.02±4.13% of indomethacin release far the RMN 70, RMN 60 and RMN 55 respectively. The corresponding indomethacin values for the cecal content medium were: 70.96±18.93, 48.68±34.99, 22.47±7.90% for the RMN 70, RMN 60 and RMN 55 respectively. It is clear from the depicted data that there is a linear correlation between the measured indomethacin values after 28 hours and the carrier treatment (i.e. modification as expressed by relative methylene blue number). Indeed, linear regression analysis yielded a value of 0.999.

Modified chondroitin is suggested as a colon specific carrier due to its ability to degrade by bacteria of the rat cecal content and its disability to disintegrate in the physiological buffer. Difference between the release profiles in the PBS controls and the rat cecal content media is explained by the influence of rat cecal bacteria on the modified chondroitin carriers. In the first stage of the study, a suppression of the release was observed. This could be explained by a bacterial layer that was formed on the surface of the solid carriers, thus leading to interruption in the drug diffusion into the medium (J. W. Costerton, K.-J. Cheng, G. G. Geesey, T. I. Ladd, I. C. Nickel, M. Dasgupta, and T. J. Marrie, *Ann. Rev. Microbiol.* 41:435–464, (1987)). When the cecal content was sonicated, the bacteria cells were ruptured and part of the endo-enzymes that were capable of degrading the drug carrier were released. This led to two observations: higher drug levels in the dissolution medium, and an elevation pattern which resulted in similar drug levels as measured in the control (PBS) experiments (FIG. 1). Different findings were observed when the dissolution experiments were continued over 28 hours. In these studies a specific release of indomethacin which was achieved by the enzymes present in the rat cecal content was observed Although no clear pattern of release kinetics could be drawn, FIGS. 3–5 demonstrate that the amount of indomethacin released in the presence of rat cecal content was significantly higher than the amount released in the control experiments. The observation in which sonication causes a higher rate of modified chondroitin degradation suggests that rat cecal bacteria are responsible for the bio-erosion of the reported colonic carrier Salyers et al. have already demonstrated that chondroitin serves a substrate for human colonic anaerobic bacteroides (Salyers, A. A. *Amer. J. clin. Nutr.* 32:158–163 (1979); Salyers, A. A. et al., *J. Bacteriol.* 143:772–780 (1980)). As a comparison, the present findings expose the possibility that bacteria are able to digest modified chondroitin as well, in a solid form, although at a much slower rate. It should be noted that the use of a sparingly soluble drug model is essential when the concept of specific degradation of drug carrier is analyzed. The use of highly soluble drug would make it complicated to distinguish whether the observed release kinetics is a result of diffusion or erosion of the drug carrier After 28 hours, the total amount of indomethacin released in the cecal medium is proportional to the relative methylene blue number of the chondroitin, or in other words, it is inversely proportional to the degree of treatment which the chondroitin has passed. This observation indicates that an optimization of the control of drug release can be achieved by balancing the reaction procedure.

This study indicates that matrices of modified chondroitin can serve as a specific colonic delivery system. Modified chondroitin has the ability to retain its drug content for over 10 hours at pH values that match the physiologic pH of the small intestine. In addition, the formulation technique which is presented in this study permits incorporation of any drug which is suitable for delivery to the large bowel. Proper examples can be drugs for the treatment of inflammatory bowel diseases such as steroids, or salicylate derivatives such as 5-amino salicylic acid. Based on the hypothesis that protein drugs are less susceptible to proteolytic degradation in the colon (M. A. Longer, J. F. Woodley, R. Duncan, *Proceed. Int. Symp. Control. Rev. Bioactive Mater*, 16:225 (1989)), modified chondroitin can serve as a proper carrier for that purpose. Drugs that possess improved colonic absorption (J. W. Fara In: L. F. Prescott and W. S. Nimmo (eds) *Novel Drug Delivery*, John Willey & Sons, Chichester, 1989, pp. 103–112) may preferably be formulated into specific colonic carrier such as the modified chondroitin.

B. In Vitro Studies with Modified Pectin

Pectic salt, as obtained in Example 5(B), was mixed with indomethacin at a ratio of 9:1 and pressed into 200 mg tablets at 2.5 tons under dry atmosphere. Indomethacin was used as a drug model because of ifs relative low solubility in the pH range of 6–7.

The specific degradability of the indomethacin carrier was studied by performing dissolution tests in: (a) specific pectinolytic enzyme (Pectinex 3X, Novo Ferment, Switzerland), and (b) phosphate buffered saline (PBS, pH 7.0) containing rat cecal content. In the first set of studies the matrices were immersed for 72 hours in 25 ml of 30,000 U of the buffered enzyme. Samples (1 ml) were withdrawn in duplicate at predetermined time intervals, and diluted in 10 ml with phosphate buffer (pH 8) for indomethacin assay. In the second set of studies the dissolution experiments were performed in PBS at 37° C., under $CO_2$, atmosphere, with the addition of pooled rat cecal content. 1 ml samples were withdrawn in duplicate at predetermined time intervals for indomethacin assay. The experiments were repeated at least 3 times. Each study was paralleled with a control experiment which did not contain enzymes or cecal content.

Samples (1 ml) were acidified (300 ml of 0.4N HCl) and extracted with 1 ml of ethylacetate containing 0.2 mg % of flufenamic acid as internal standard. The mixture was vortexed and centrifuged. 500 ml of the organic phase was evaporated, and redissolved in the mobile phase. Twenty microliters of the solution were injected into the HPLC system and detected at 280 nm. HPLC conditions: column; RP-18 (5 micron, 250×4.6 mm); mobile phase. acetonitrile/ Phosphate buffer pH 7.5 (50:50).

Figure 7:
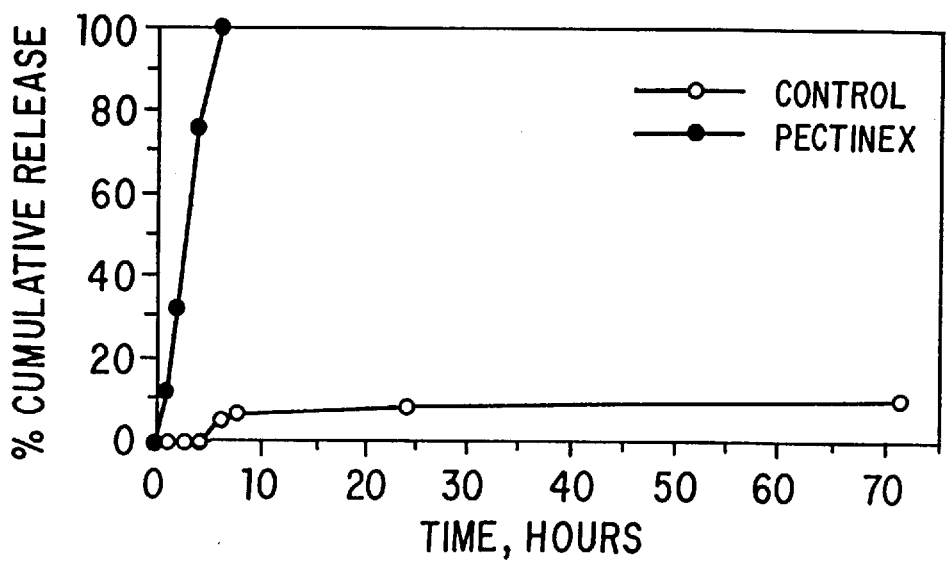
FIG. 7: Cumulative release of indomethacin from pectic salt matrix with and without pectinolytic enzyme.
Figure 8:
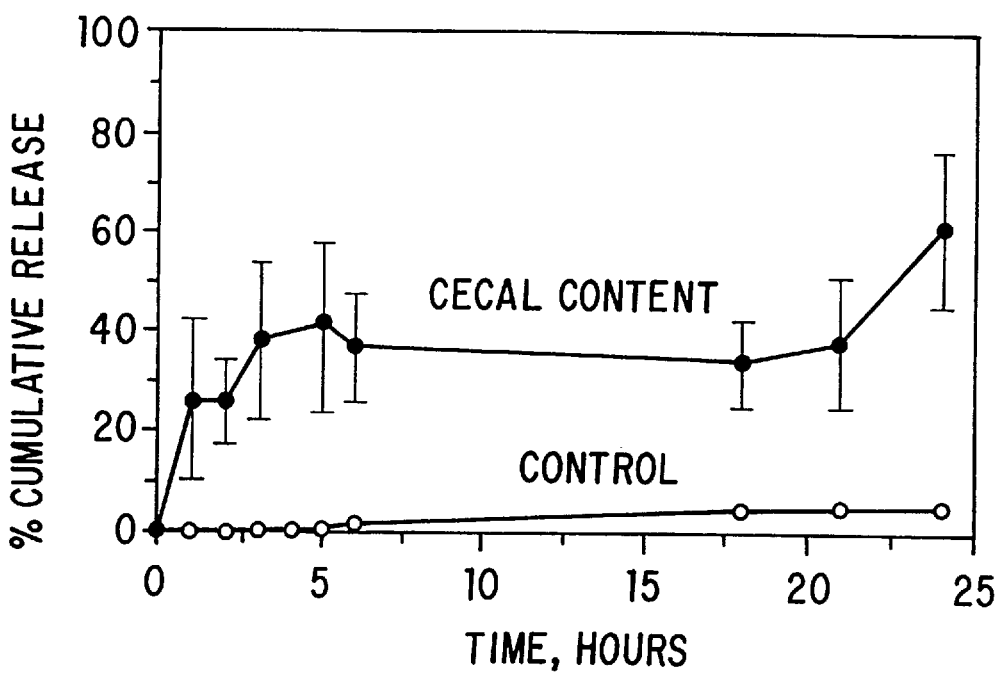
FIG. 8: Cumulative release of indomethacin from pectic salt matrices in the presence of rat cecal content as compared to its release in PBS (control) dissolution medium.

The results are summarized in FIGS. 7 and 8. It is clear—both in the case of the pectinolytic enzyme and in those experiments that involved rat cecal content—that indomethacin was released specifically and significantly faster as compared to the control studies. These observations were verified by weighing the dry residues of the matrices at the end of each experiment. Only 16.88±0.3% of the initial weight was left at the end of the control dissolution studies of the rat cecal content experiments. This observation may suggest that indomethacin is attached to the matrices' debris much longer after the delivery system has disintegrated. In other words, despite the increase in the surface area of the particles caused by the tablet disintegration, indomethacin was not released as expected because it was not released from the fine particles of the pectic salt. The specific degradation of the whole carrier is assumed to be caused by enzymes originating from the rat cecal bacteria and it is concluded that the pectic salt can serve as a colon-specific delivery system.

It should be noted that by using various calcium (or other metal) pectin salts with different solubility properties as the matrices [reference is made to Example 5(B)], the rate of drug release can be controlled and adjusted.

EXAMPLE 7

In Vivo Studies with Modified Chondroitin

Chondroitin sulfate type A (Sigma U.S.A.) was treated as described above [Example 5(A)(2)]. The characterization of the modified product was performed by its methylene blue adsorption. The products in dialysis bag were dipped in 0.1% methylene blue solution. The decrease in the dye concentration was monitored at 685 nm. The adsorption capability of the product was defined as the Relative Methylene Blue Number (RMN). Matrices were prepared by mixing indomethacin and modified chondroitin at a ratio of 1:9 and manually pressed.

The in vitro release experiments were performed in phosphate buffered saline (PBS) with or without the addition of rat cecal content. The dissolution beakers were shaken in a 37° C. water bath (80 rpm) under $CO_2$ atmosphere. Samples were withdrawn in triplicate at predetermined time intervals for indomethacin analysis. The experiments were repeated 3 times for each formulation.

A study was conducted in one cannulated dog (A. Rubinstein, V. H. Kin Li, P. Gruber, P. Bass, and J. R. Robinson, *J. Pharmacol. Methods*. 19:213–217 (1988)), using formulation RMN 60. In this study the chondroitin formulation was administered directly into the distal portion of the dog small intestine. As a control, hydroalcoholic dispersion of indomethacin was used. Plasma samples (8 ml) were withdrawn from the cephalic vein, out of which 1 ml samples were taken for indomethacin analysis.

Indomethacin analysis: Aliquot were extracted in the presence of flufenamic acid as an internal standard. The extracting solvent was ethylacetate in the dissolution samples and ethyl ether in the plasma samples. After acidifying, 20 microliters of the organic phase were injected into the HPLC system and detected at 280 nm.

Figure 9:
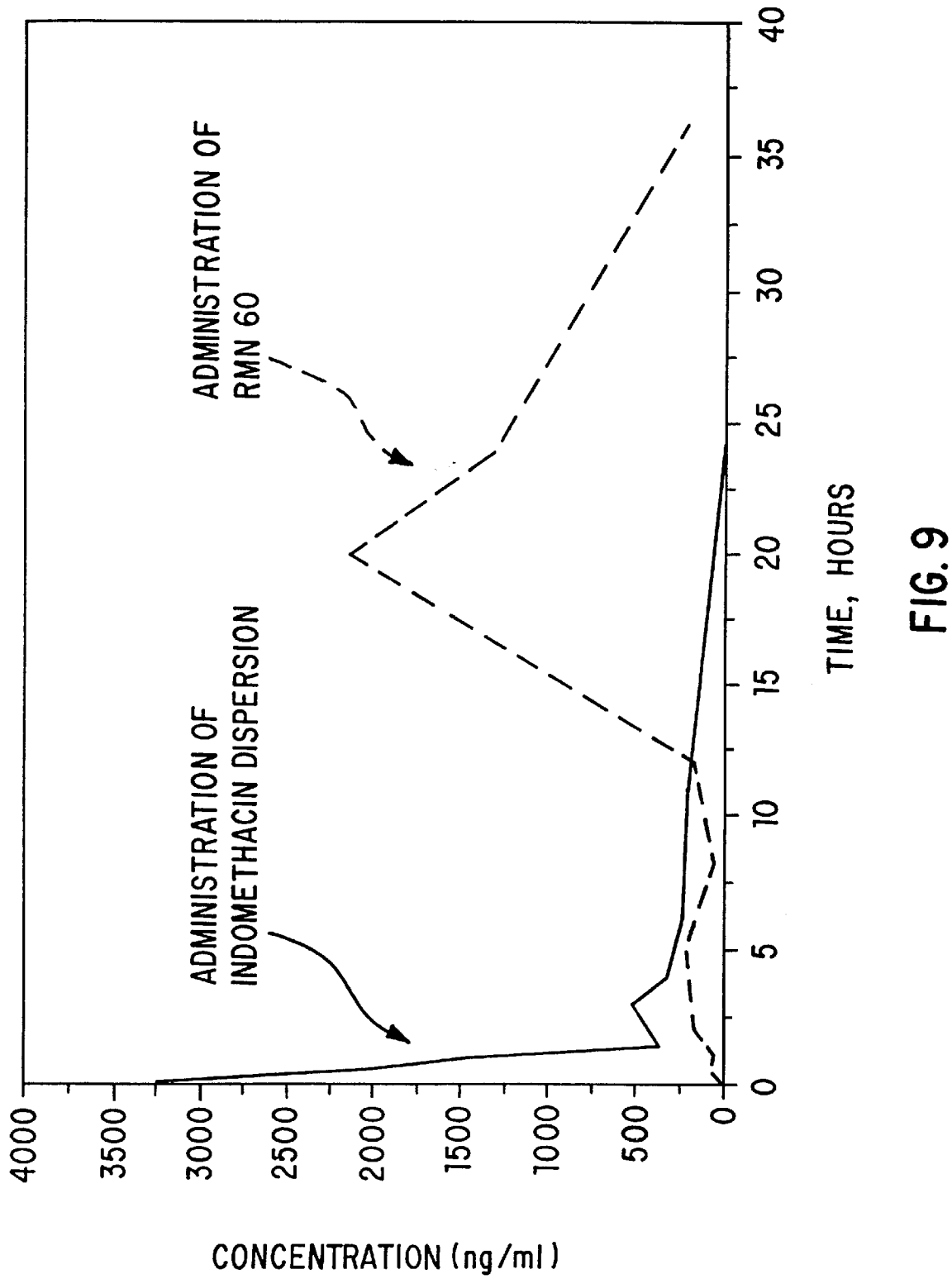
FIG. 9: Plasma levels of indomethacin after intra-intestinal administration of modified chondroitin colonic delivery system and hydroalcoholic dispersion in dog.

The in vitro results are shown in FIG. 6. This figure demonstrates that the indomethacin cumulative release after 28 hours was linearly proportional to the degree of carrier modification as expressed by the RMN. A significant difference ($p<0.05$) was observed between the dissolution in the cecal content and that in the PBS control. The pharmacokinetic profiles of indomethacin in the cannulated dog plasma are presented in FIG. 9. While indomethacin was rapidly absorbed from the site of administration, when given as dispersion, the indomethacin of the colonic chondroitin system manifested a similar extent of absorption, with a 10 hour delay. In view of the above in vitro experiments which demonstrate that the dissolution of the formulation is limited in physiological buffer, the in vivo results indicate bacterial degradation of the developed colonic carrier in the dog large bowel. Therefore, the modified chondroitin appears to be effective as an orally administered colonic drug delivery carrier.

Having now fully described the invention, it will be understood by those with skill in the art that the invention may be performed within a wide and equivalent range of conditions, parameters and the like, without affecting the spirit or scope of the invention or any embodiment thereof. All references cited herein are incorporated herein fully by reference.

What is claimed is:

1. A colonic delivery system for oral administration of a drug to a patient in need of such drug, wherein said system comprises said drug in combination with a matrix, said matrix comprises a saccharide-containing polymer, said saccharide-containing polymer is enzymatically degraded in the colon by bacteria located therein such that said matrix is degraded in the colon and said drug preferentially released therein, and wherein said drug in combination with said matrix is coated with a biodegradable polymeric coating.

2. The colonic delivery system of claim 1, wherein said polymer that comprises said matrix is a modified natural saccharide-containing polymer.

3. The colonic delivery system of claim 2, wherein said natural saccharide-containing polymer is a mucopolysaccharide.

4. The colonic delivery system of claim 2, wherein said modified natural saccharide-containing polymer is cross-linked chondroitin sulfate.

5. The colonic delivery system of either of claims 1 or 2, wherein said drug comprises indomethacin.

6. The colonic delivery system of claim 4, wherein said drug comprises indomethacin.

7. The colonic delivery system of claim 2, wherein said modified natural saccharide-containing polymer is a metal salt of pectin.

8. The colonic delivery system of claim 7, wherein said metal is calcium.

9. The colonic delivery system of either of claims 1 or 2, wherein said drug comprises an anti-inflammatory agent.

10. The colonic delivery system of claim 9, wherein said anti-inflammatory agent is a nonsteroidal anti-inflammatory agent.

11. The colonic delivery system of claim 9, wherein said anti-inflammatory agent is a steroidal anti-inflammatory agent.

12. The colonic delivery system of either of claims 1 or 2, wherein said drug is selected from the group consisting of dexamethasone, budesonide, beclomethasone, flucticasone, tioxocortal, and hydrocortisone.

13. The colonic delivery system of either of claims 1 or 2, wherein said drug is cyclospori.

14. The colonic delivery system of either of claims 1 or 2, wherein said drug is selected from the group consisting of theophylline, nifedipine, isosorbide dinitrate and oxprenolol.

15. The colonic delivery system of either of claims 1 or 2, wherein said drug is an antispasmodic agent for the treatment of Irritable Bowel Syndrome.

16. The colonic delivery system of claim 15, wherein said drug is cimetropium bromide.

17. The colonic delivery system of either of claims 1 or 2, wherein said drug is an anti-neoplastic agent.

18. The colonic delivery system of claim 17, wherein said anti-neoplastic agent is selected from the group consisting of methotrexate, tamoxifen, cyclophosphamide, mercaptopurine and etoposide.

19. A method of delivering a drug to the colon of a patient in need of such drug, wherein said method comprises oral administration of the colonic delivery system of either of claims 1 or 2.

20. The colonic delivery system of claim 2, wherein said polymer that comprises said matrix is modified to reduce hydrophilicity.

21. The colonic delivery system of claim 20, wherein said modification is by cross-linking.

22. The colonic delivery system of claim 1, wherein said matrix is resistant to the stomach enzymes and stomach pH of said patient.

23. The colonic delivery system of claim 1, wherein said matrix is resistant to enzymes of the small intestine of said patient.

24. The colonic delivery system of claim 1, wherein said polymer comprises a synthetic polymer.

25. The colonic delivery system of claim 24, wherein said synthetic polymer comprises a methacrylic polymer.

26. The colonic delivery system of claim 25, wherein said synthetic polymer further comprises an oligosaccharide.

27. The colonic delivery system of claim 26 wherein said oligosaccharide is resistant to the enzymatic action of enzymes in the small intestine of said patient.

28. The colonic delivery system of claim 26 wherein said oligosaccharide is chosen from the group consisting of cellobiose, lactulose, raffinose, and stachyose.

* * * * *